United States Patent
Riedel

(10) Patent No.: US 11,844,936 B2
(45) Date of Patent: Dec. 19, 2023

(54) MEDICAMENT DELIVERY DEVICE

(71) Applicant: Sanofi, Paris (FR)

(72) Inventor: Stephan Riedel, Frankfurt am Main (DE)

(73) Assignee: Sanofi, Paris (FR)

( * ) Notice: Subject to any disclaimer, the term of this patent is extended or adjusted under 35 U.S.C. 154(b) by 441 days.

(21) Appl. No.: 17/253,705

(22) PCT Filed: Jun. 25, 2019

(86) PCT No.: PCT/EP2019/066814
§ 371 (c)(1),
(2) Date: Dec. 18, 2020

(87) PCT Pub. No.: WO2020/002321
PCT Pub. Date: Jan. 2, 2020

(65) Prior Publication Data
US 2021/0346609 A1    Nov. 11, 2021

(30) Foreign Application Priority Data

Jun. 25, 2018  (EP) ..................... 18305804

(51) Int. Cl.
*A61M 5/32*   (2006.01)
*A61M 5/20*   (2006.01)
(Continued)

(52) U.S. Cl.
CPC ............. *A61M 5/326* (2013.01); *A61M 5/20* (2013.01); *A61M 5/24* (2013.01); *A61M 5/321* (2013.01);
(Continued)

(58) Field of Classification Search
CPC ........ A61M 5/326; A61M 5/20; A61M 5/373; A61M 5/3213; A61M 2005/3247;
(Continued)

(56) References Cited

U.S. PATENT DOCUMENTS

| 5,368,577 A | 11/1994 | Teoh et al. |
| 6,117,110 A | 9/2000 | Radmand |

(Continued)

FOREIGN PATENT DOCUMENTS

| CN | 101909526 | 12/2010 |
| CN | 103249443 | 8/2013 |

(Continued)

OTHER PUBLICATIONS

PCT International Preliminary Report on Patentability in International Application No. PCT/EP2019/066814, dated Dec. 29, 2020, 7 pages.

(Continued)

*Primary Examiner* — Brandy S Lee
*Assistant Examiner* — Kathleen Paige Farrell
(74) *Attorney, Agent, or Firm* — Fish & Richardson P.C.

(57) ABSTRACT

The present invention relates to a medicament delivery device, comprising an outer body, a receptacle for a medicament, a needle for the administration of the medicament, an injection mechanism with an actuating mechanism for injecting the medicament into the patients body, and a needle guard for the needle. The medicament delivery device further comprising a detecting element for the detection of the orientation of the medicament delivery device, and a locking mechanism releasing the actuating mechanism, if the detecting element is in the at least first position, and locking the actuating mechanism, if the detecting element is in the at least second position, wherein the locking mechanism is controlled and/or actuated by the detecting element.

20 Claims, 2 Drawing Sheets

(51) Int. Cl.
    *A61M 25/06*     (2006.01)
    *B65D 83/56*     (2006.01)
    *A61M 5/24*     (2006.01)

(52) U.S. Cl.
CPC ....... *A61M 5/3213* (2013.01); *A61M 25/0631* (2013.01); *A61M 2005/208* (2013.01); *A61M 2005/2013* (2013.01); *A61M 2005/2073* (2013.01); *A61M 2005/325* (2013.01); *A61M 2005/3247* (2013.01); *A61M 2005/3267* (2013.01); *A61M 2205/215* (2013.01); *B65D 83/565* (2015.07)

(58) Field of Classification Search
CPC ............ A61M 2005/2073; A61M 5/24; A61M 25/0631; A61M 5/321; A61M 2005/325; A61M 2205/215; A61M 2005/208; B65D 83/565

See application file for complete search history.

(56) References Cited

U.S. PATENT DOCUMENTS

| | | | |
|---|---|---|---|
| 2001/0013525 A1 | 8/2001 | Ritsche et al. | |
| 2002/0177808 A1 | 11/2002 | Carmel | |
| 2013/0138048 A1 | 5/2013 | Kemp et al. | |
| 2016/0136359 A1 | 5/2016 | Wong | |
| 2020/0016333 A1* | 1/2020 | Soares et al. | A61M 5/158 |
| 2020/0114090 A1* | 4/2020 | Mannochio et al. | A61M 5/3202 |
| 2023/0090661 A1* | 3/2023 | Jensen et al. | A61M 5/3146 |

FOREIGN PATENT DOCUMENTS

| | | |
|---|---|---|
| CN | 103648553 | 3/2014 |
| CN | 104780961 | 7/2015 |
| EP | 2364740 | 9/2011 |
| EP | 2923714 | 9/2015 |
| EP | 2944340 | 11/2015 |
| JP | H11-137679 | 5/1999 |
| JP | 2004-527335 | 9/2004 |
| JP | 2017-205556 | 11/2017 |
| WO | WO 2002/094356 | 11/2002 |
| WO | WO 2009/088430 | 7/2009 |
| WO | WO 2012/045831 | 4/2012 |
| WO | WO 2012/152666 | 11/2012 |
| WO | WO 2013/138549 | 9/2013 |
| WO | WO 2014/040985 | 3/2014 |

OTHER PUBLICATIONS

PCT International Search Report and Written Opinion in International Application No. PCT/EP2019/066814, dated Aug. 7, 2019, 10 pages.

* cited by examiner

MEDICAMENT DELIVERY DEVICE

TECHNICAL FIELD

The invention relates to a medicament delivery device.

BACKGROUND OF THE INVENTION

Medicament delivery devices typically fall into two categories—manual devices and autoinjectors. In a conventional manual device, manual force is required to drive a medicament through a needle. This is typically done via a button or a plunger that has to be continuously pressed during the injection. Autoinjector devices aim to make self-injection easier for patients. A conventional autoinjector may provide the force for administering the injection by a spring, and a trigger button, a needle guard or other mechanism may be used to activate the injection. Autoinjectors may be single-use or reusable devices.

However, administering a medicament by injection is a process which presents a number of risks and challenges for patients and healthcare professionals.

An analyze of the handling of medicament delivery devices, in particular of autoinjector devices, by patients have shown that some users have held the autoinjector in a wrong orientation. They pressed with their thumb against the needle cover of the autoinjector and tried to activate the device by pressing the activation button against the injection site. This in most cases has led to a needle stick injury into the thumb.

Consequently, improper handling of a medicament delivery device, specially a wrong orientation of the device, may easily result in needle stick injuries.

Thus, there is a need for a medicament delivery device that protects the patient or user from injury, particularly from needle stick injuries.

SUMMARY

It is an object of the present invention to provide an improved medicament delivery device having a reduced risk for needle stick injuries.

This object is achieved by a medicament delivery device according to claim 1. Embodiments are subject of the dependent claims.

According to the present invention, there is provided a medicament delivery device comprising an outer body, a receptacle for a medicament to be administered, a needle for the administration of the medicament into a patient's body, a needle guard for the needle, the needle guard having a needle opening for the needle at its distal end, and comprising an actuating mechanism for moving the needle and/or the receptacle and/or the needle guard in an axial direction of the medicament delivery device.

The medicament delivery device further comprising a detecting element for the detection of the orientation of the medicament delivery device, the detecting element being movable between at least a first position and at least a second position, wherein the detecting element takes the at least first position, if the medicament delivery device is held by a user in an orientation in which the medicament delivery device is usable for injecting the medicament into the patient's body, and wherein the detecting element takes the at least second position, if the medicament delivery device is held by the user in an orientation in which the medicament delivery device should not be used, and/or is in a configuration not intended for use, for injecting the medicament into the patient's body. In addition to that, the medicament delivery device further comprising a locking mechanism releasing the actuating mechanism, if the detecting element is in the at least first position, and locking the actuating mechanism, if the detecting element is in the at least second position.

The detecting element and the locking elements ensure that a user of the medicament delivery device can no longer be injured by the needle if the medicament delivery device is not held properly or attached to the body of the patient in a wrong orientation.

If the medicament delivery device is held by a user in an orientation in which the medicament delivery device should not be used, or if the device is in a configuration not intended for use, e.g. if the device is held in an orientation in which the proximal end of the medicament delivery device is facing the injection site of the patient's body, and the distal end, with the injection needle and the needle opening, is facing the user's hand or thumb, the detecting element takes the at least second position and the locking mechanism prevents the needle from coming out of the needle opening of the device. This, because the locking mechanism is locking the actuating mechanism. The hand or the thumb of the user are not able to get into contact with the needle.

If, however, the medicament delivery device is held and used correctly, e.g. if the device is held in an orientation in which the distal end of the medicament delivery device, with the injection needle and the needle opening, is facing the injection site of the patient's body, and the proximal end is facing the user's hand or thumb, the detecting element takes the at least first position and the needle is able to inject the medicament into the patient's body. This because the locking mechanism is releasing the actuating mechanism and allowing the needle to move through the needle opening of the device. The hand or the thumb of the user are not able to get into contact with the needle too.

The locking mechanism is movable between a release position and a locking position, wherein the locking mechanism takes the release position, if the detecting element is in the at least first position, and wherein the locking mechanism takes the locking position, if the detecting element is in the at least second position.

The detection element thus recognizes the orientation of the medicament delivery device and controls and/or activates the locking mechanism as soon as the device is to be handled incorrectly. If the medicament delivery device is used correctly, the detection element remains in its first position and the device can be used normally.

Another aspect of the invention contributes to this too, if the locking mechanism of the medicament delivery device, in the release position, is not in engagement with the actuating mechanism. While on the other hand the locking mechanism, in the locking position, is in engagement with the actuating mechanism.

Consequently, the detection element and the locking mechanism provide together an orientation safeguarding for the medicament delivery device, wherein the locking mechanism is controlled and/or actuated by the detecting element.

If the medicament delivery device is properly held or used, an injection can be made by the needle into the patient's body. However, if the medicament delivery device is improperly held or handled, the orientation safeguarding prevents that the patient or the user is getting into contact with the needle, because the needle is not able to protrude from the needle opening.

In one embodiment of the invention, the locking mechanism is controlled by the detecting element electronically and/or magnetically. In such an embodiment, the detecting element may be an electronic or magnetic sensor. This sensor is sensing the orientation of the medicament delivery device relative to a vertical direction and/or relative to the body of a patient. Furthermore, this sensor is adapted to control the locking mechanism via electronic or magnetic means.

In another embodiment of the invention, the locking mechanism is controlled by the detecting element mechanically, wherein the detecting element is a mechanical sensor and actuator. This sensor and actor is sensing the orientation of the medicament delivery device relative to a vertical direction and/or relative to the body of a patient. Furthermore, this sensor and actor is adapted to control the locking mechanism via mechanical means.

In yet another embodiment of the invention, the locking mechanism is controlled by an electro-mechanical detecting element. In such an embodiment, the detecting element may be an electronic, magnetic or mechanical sensor. This sensor is sensing the orientation of the medicament delivery device relative to a vertical direction and/or relative to the body of a patient. Furthermore, this sensor is adapted to control the locking mechanism via mechanical or electronic means.

The detection element may be positioned within or at the outer body.

Constructively it is favorable, if the locking mechanism has at least one locking element, each locking element being movable between the release position and the locking position.

Each locking element is a detent, a ratchet, a latch or the like.

Each locking element is mounted rotatable or pivotally within the outer body.

The locking elements can be arranged within the outer body of the medicament delivery devise opposite to one another. But, they can also be arranged circular and with equidistant distances to each other within the outer body.

In order that the locking elements of the locking mechanism always intervene reliable, the actuating mechanism has a recess, an undercut, a step, or the like for the engagement of, or for receiving each locking element, wherein each locking element is in engagement with the recess, the undercut, the step, or the like, when the locking elements have been moved into the locking position.

In a further aspect of the invention, the locking mechanism of the medicament delivery device is actuated by the detecting element, when the detecting element is moving from the at least first position into the at least second position.

All this allows a particularly compact design of the medicament delivery device which is always able to work reliable.

Each locking element is brought into its respective locking position and into the engagement with the actuating mechanism by the detecting element, wherein the detecting element is, in the at least second position, securing and/or fixing the locking elements in their locking position.

The detecting element has an opening with a face, which interacts with the locking elements, when the detecting element moves from the first position to the second position.

The detecting element, in the at least second position, is enclosing the locking elements in their locking position.

The detection element thus assumes two functions: It detects if the device is held by the user in a correct or incorrect orientation or position. If there is a risk of the user injuring himself on the needle, because he is using the device in wrong orientation or manner, the detection element actuates the locking elements and prevents the needle from escaping from the needle opening.

The detecting element may be a collar or a ring.

The detecting element may be driven or moved by gravity.

In addition or alternatively, the locking elements may be driven by the detecting element against a reset force.

In one embodiment of the invention, the receptacle and the needle may form a syringe, wherein the syringe being movable by or within the actuating mechanism in the axial direction of the medicament delivery device in order to administrate the medicament into the patient's body. In these embodiments, the needle guard for the needle is often an integral part of the outer body so that the needle opening for the needle is formed in the distal end of the outer body and the outer body itself is acting as a needle guard.

If such a medicament delivery device—e.g. a safety syringe—is held by a user in a wrong orientation, e.g. that the proximal end of the medicament delivery device is facing the injection site of the patient's body, and the distal end, with the injection needle and the needle opening, is facing the user's hand or thumb, the detecting element takes the at least second position and the locking mechanism locks the actuation mechanism, so that the syringe is not able to move forward, and the needle is not able to move out of the needle opening. The hand or the thumb of the user are not able to get injured at the needle tip.

If, however, this medicament delivery device is held and used correctly, the detecting element takes the at least first position and the locking mechanism is not locking the actuating mechanism. The syringe is able to move forward and to inject the medicament into the patient's body via the needle. This, because the locking mechanism is releasing the actuating mechanism and allowing the syringe to move.

In another embodiment, the syringe may be a part of the actuating mechanism, wherein the locking mechanism releasing the movement of the syringe, if the detecting element is in the at least first position, and locking the movement of the syringe, if the detecting element is in the at least second position.

In one embodiment of the invention, the medicament delivery device is an autoinjector, wherein the needle guard is a part of the actuating mechanism and being movable in the axial direction relative to the outer body, and wherein the locking mechanism releasing the movement of the needle guard, if the detecting element is in the at least first position, and locking the movement of the needle guard, if the detecting element is in the at least second position.

If such an autoinjector is held by a user in a wrong orientation, e.g. that the proximal end of the medicament delivery device is facing the injection site of the patient's body, and the distal end, with the injection needle, the needle guard and the needle opening, is facing the user's hand or thumb, the detecting element takes the at least second position and the locking mechanism locks the needle guard, so that it is not able to be pushed into the outer body. The needle is not able to move out of the needle opening. The hand or the thumb of the user is not able to get injured at the needle.

If, however, the autoinjector is held and used correctly, the detecting element takes the at least first position and the autoinjector can be pressed with the distal end of the needle guard against the injection site of the patient's body. The actuating mechanism and the needle guard are not locked by the locking mechanism. The needle guard is able to move into the outer body and to activate the injection mechanism of the syringe so that the needle is able to inject the medicament into the patient's body.

However, the orientation safeguarding system as described above for a medicament delivery device—provided by the detecting element and the locking mechanism—can be used in both systems, manual devices and autoinjectors. In particular, the detecting element and the locking mechanism can be used in all injection devices with a (movable) needle guard.

In another embodiment of the invention, a system comprises a medicament delivery device as described above, and comprising a receptacle, namely in form of a primary container, mounted in the medicament delivery device, wherein said primary container is filled with the medicament to be administered.

One realizes that the medicament delivery device and the system according to the invention comprise a control and locking mechanism for safely handling and for a safely using the medicament delivery device, with a reduced risk for needle stick injuries.

In the following text, a set of particularly advantageous aspects of the medicament delivery device and the system comprising a medicament delivery device are provided by making use of numbers to facilitate making references to the respective aspects. The scope of the protection is, however, defined by the appended claims.

1. A medicament delivery device comprising:
    an outer body,
    a receptacle for a medicament to be administered,
    a needle for the administration of the medicament into a patient's body,
    a needle guard for the needle, the needle guard having a needle opening for the needle at its distal end, and
    an actuating mechanism for moving the needle and/or the receptacle and/or the needle guard in an axial direction of the medicament delivery device,
the medicament delivery device further comprising:
    a detecting element for the detection of the orientation of the medicament delivery device,
        the detecting element being movable between at least a first position and at least a second position,
        wherein the detecting element takes the at least first position, if the medicament delivery device is held by a user in an orientation in which the medicament delivery device is usable for injecting the medicament into the patient's body, and
        wherein the detecting element takes the at least second position, if the medicament delivery device is held by the user in an orientation in which the medicament delivery device should not be used, and/or is in a configuration not intended for use, for injecting the medicament into the patient's body, and
    a locking mechanism releasing the actuating mechanism, if the detecting element is in the at least first position, and locking the actuating mechanism, if the detecting element is in the at least second position.
2. The medicament delivery device according to aspect 1, characterized in that the locking mechanism is movable between a release position and a locking position,
    wherein the locking mechanism takes the release position, if the detecting element is in the at least first position, and
    wherein the locking mechanism takes the locking position, if the detecting element is in the at least second position.
3. The medicament delivery device according to any one of the aspects 1 or 2, characterized in that the locking mechanism, in the release position, is not in engagement with the actuating mechanism, and that the locking mechanism, in the locking position, is in engagement with the actuating mechanism.
4. The medicament delivery device according to any one of the preceding aspects, characterized in that the locking mechanism is controlled and/or actuated by the detecting element.
5. The medicament delivery device according to any one of the preceding aspects, characterized in that the locking mechanism has at least one locking element, each locking element being movable between the release position and the locking position.
6. The medicament delivery device according to aspect 5, characterized in that each locking element is a detent, a ratchet, a latch or the like, wherein each locking element is mounted rotatable or pivotally within or at the outer body.
7. The medicament delivery device according to any one of the aspects 5 to 6, characterized in that the actuating mechanism has a recess, an undercut, a step, or the like for the engagement of, or for receiving each locking element, wherein each locking element is in engagement with the recess, the undercut, the step, or the like, when the locking elements have been moved into the locking position.
8. The medicament delivery device according to any one of the aspects 5 to 7, characterized in that each locking element is brought into its respective locking position and into the engagement with the actuating mechanism by the detecting element.
9. The medicament delivery device according to any one of the aspects 5 or 8, characterized in that the detecting element has an opening with a face, which interacts with the locking elements, when the detecting element moves from the first position to the second position.
10. The medicament delivery device according to any one of the aspects 5 to 9, characterized in that the detecting element, in the at least second position, is enclosing the locking elements in their locking position.
11. The medicament delivery device according to any one of the aspects 1 to 10, characterized in that the detecting element is a collar or a ring, wherein the detecting element is driven or moved by gravity.
12. The medicament delivery device according to any one of the aspects 1 to 11, characterized in that the receptacle and the needle form a syringe, the syringe being movable by the actuating mechanism in the axial direction of the medicament delivery device, wherein the needle guard for the needle is an integral part of the outer body, and that the needle opening for the needle is at the distal end of the outer body.
13. The medicament delivery device according to any one of the aspects 1 to 11, characterized in that the medicament delivery device is an autoinjector.
14. The medicament delivery device according to aspect 1, characterized in that the needle guard is a part of the actuating mechanism and being movable in the axial direction relative to the outer body, wherein the locking mechanism releasing the movement of the needle guard, if the detecting element is in the at least first position, and locking the movement of the needle guard, if the detecting element is in the at least second position.
15. A system comprising a medicament delivery device according to any one of the preceding aspects, and comprising the receptacle, namely in form of a primary container, mounted in the medicament delivery device, wherein said primary container is filled with the medicament to be administered.

BRIEF DESCRIPTION OF THE FIGURES

Further features, details and advantages of the present invention will become apparent from the wording of the patent claims and from the following description of exemplary embodiments with reference to the drawings. They show in FIG. 1 a schematic sectional view of a part of a medicament delivery device, which is held in a correct orientation, and FIG. 2 a schematic sectional view of the medicament delivery device of FIG. 1, which is held in a wrong orientation.

DETAILED DESCRIPTION

The use of the term "proximal" with respect to the medicament delivery device or a component thereof, always refers to a direction, a portion, an end, or the like which is—under regular use of the medicament delivery device—directed or located away or farthest away from the medicament delivery site of the patient.

The use of the term "distal" with respect to the medicament delivery device or a component thereof, always refers to a direction, a portion, an end, or the like which is—under regular use of the medicament delivery device—directed or located towards or closest to the medicament delivery site of the patient.

Figure 1:
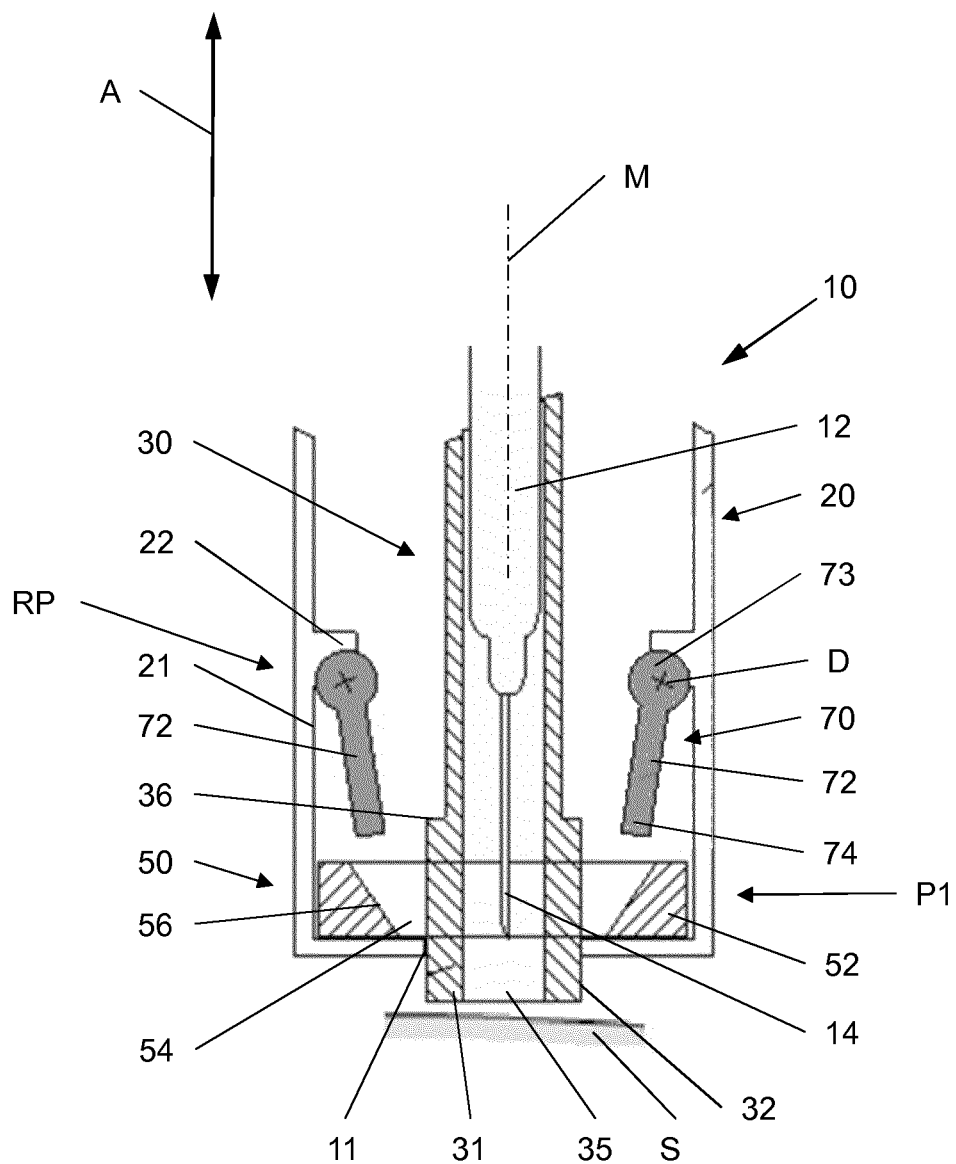
Figure 2:
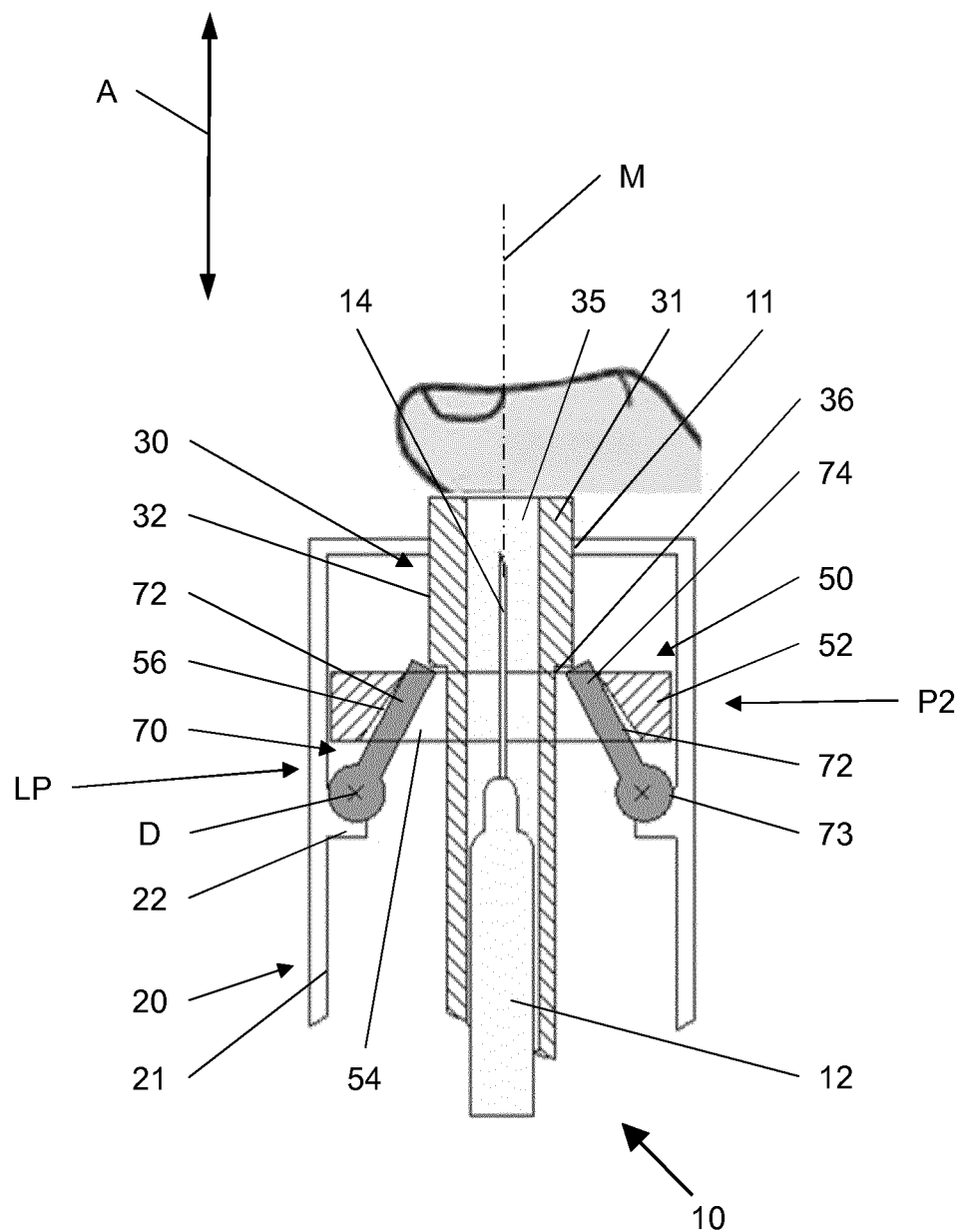

FIGS. 1 and 2 schematically show the basic principle of an orientation safeguarding for a medicament delivery device 10 comprising a detection element 50 and a locking mechanism 70.

In an embodiment of the invention, the medicament delivery device 10 is designed as a manual device.

This device typically has an outer body 20, a receptacle 12 for a medicament to be administered, e.g. a syringe or a cartridge, and a needle 14, provided at the distal end of the device 10. The receptacle 12 and the needle 14 preferably form a syringe, wherein the syringe is mounted movable within the outer body and being driven by an actuating mechanism (not shown) in the axial direction A of the outer body 20.

If the device 10 is not in use, the syringe is in a proximal position and the needle 14 is hidden by a needle guard 30. This needle guard 30 is an integral part of the outer body 20, which forms at its distal end a needle opening 35 for the needle 14.

If the device 10 is in use, the syringe is moving forward and the needle 14 is protruding out of the needle opening 35 in order to administer the medicament into the patient's body.

In another embodiment of the invention, the medicament delivery device 10 is designed as an autoinjector.

Such a device 10 typically has an outer body 20 being adapted to hold a medicament receptacle 12, such as a syringe. The syringe may be a pre-filled syringe having a needle 14 arranged at a distal end of the device 10. The needle 14 is normally protected by a needle sheath (not shown). The medicament receptacle 12 may also be a cartridge which includes the medicament and engages a removable needle 14.

The autoinjector 10 further comprises a needle guard 30 with a needle opening 35 at its distal end 31. This needle guard 30 has two functions: Before the use of the autoinjector 10, the user activates the device by pressing the needle guard 30 with its distal end against the injection site. After the use of the device 10, the needle guard 30 locks with the outer body and protects the user against a needle stick injury.

Consequently, the needle guard 30 is designed to cover the needle 14 when the medicament delivery device 10 is not in use for injecting the medicament. The needle guard 30 is telescoped within the outer body 20 and a guard spring (not shown) is arranged to bias the needle guard 30 in a distal direction against the outer body 20. In its initial position, the needle guard 30 protrudes with its distal end 31 through an opening 11 at the distal front end of the outer body 20. After the injection the outer part of the needle guard 30 is longer and covers the needle 14.

In order to automatically administer the medicament with the medicament delivery device 10, an injection mechanism is provided (not shown). This mechanism has for example a piston within the outer body 20, which is driven by a spring.

A plunger release mechanism (also not shown) is arranged within the outer body 20 for preventing release of the plunger prior to retraction of the needle guard 30 relative to the outer body 20, and for releasing the plunger once the needle guard 30 is sufficiently retracted.

The triggering of the injection mechanism takes place with an actuating mechanism. This mechanism may comprise either a trigger element (not shown) or the needle guard 30 is used as the trigger element.

For the administration of the medicament to the patient, the autoinjector 10 is—after removing a protective cap (not shown)—placed at the injection site on the patient's skin S with the distal end 31 of the needle guard 30.

Further details and particularities of autoinjectors are described for example in the Applicant's patent applications EP 2 923 714 A1 and EP 2 944 340 A1, which are hereby incorporated by reference in their entirety and to which reference is hereby made in their entirety.

All embodiments of a medicament delivery device 10 have in common an orientation safeguarding as shown in FIGS. 1 and 2 and further described below.

This orientation safeguarding is designed as a control and locking mechanism, comprising a detecting element 50 for the detection of the orientation of the medicament delivery device 10, and a locking mechanism 70 releasing or locking the actuating mechanism and/or the needle guard 30 of the medicament delivery device 10.

In an exemplary embodiment, the detection element 50 is a ring 52, which is arranged at the distal end of the outer body 20 and thus in the region of the needle guard 30. The ring 52 is seated in a defined clearance to the inner circumference 21 of the outer body 20 and is mounted longitudinally displaceable along an axial direction A of the outer body 20. The ring 52 further has a central opening 54 with an inclined face 56 directed in an angle relative to the axial direction A to the outer circumference 32 of the needle guard 30, and enclosing the needle guard 30.

The detection element 50, namely the ring 52, is movable within the outer body 20 along the axial direction A between a first position P1—shown in FIG. 1—at the distal end of the outer body 20 and a second position P2—shown in FIG. 2—in a distance (not named) proximal to the first position P1.

The locking mechanism 70 has at least one locking element 72 in form of a detent, a ratchet, a latch, or the like. Each locking element 72 has a first end 73 and a second end 74, whereby the first end 73 is mounted pivotally around an axis D at the inner circumference 21 of the outer body 20. For this purpose, the outer body 20 is for example at least partly provided with a flange, a collar 22 or the like, bearing the axis D.

The orientation of the pivot axis D is arranged such that the elements 72 can pivot radially with respect to the needle guard 30 and the central axis M of the outer body 20 between two positions RP, LP. The first position RP—shown in FIG. 1—is a releasing position in which the locking mechanism 70 and its locking elements 72 release the needle guard 30. The second position RP—shown in FIG. 2—is a locking position in which the locking mechanism 70 and its locking element 72 lock the needle guard 30.

The exemplary embodiment of FIGS. 1 and 2 shows two locking elements 72 arranged on opposite sides relative to the needle guard 30. However, it is also possible to use three or more locking elements 72, which are preferably arranged at equidistant intervals around the needle shield 30.

The latter is provided with a recess, an undercut, a step 36, or the like for the engagement of, or for receiving the second ends 74 of the locking elements 72.

If the medicament delivery device 10, whether as a manual device or as an autoinjector, is held by a user in a correct orientation, in which the medicament delivery device 10 is usable for injecting the medicament into the patient's body, i.e. the distal end 31 of the needle guard is pressed against the injection site of the patient's skin S, the detecting element 50 takes the first position P1, wherein the detecting element 50 is moved by gravity into the first position P1 at the distal end of the outer body 20.

The detection element 50 is now not in engagement with the locking elements 72 of the locking mechanism 70 and the latter are in their release position RP.

The needle guard 30 can be activated, in particular be moved in the axial direction A into the outer body 20.

If the medicament delivery device 10 is held by a user in a wrong orientation, in which the medicament delivery device 10 should not to be used for injecting the medicament into the patient's body, i.e. the proximal end of the outer body 20 is pressed against the injection site of the patient's skin S, and a thumb F of the user is pressed onto the distal end 31 of the needle guard 30, the detecting element 50 is moved by gravity into the second position P2.

As the detection element 50 is moved by gravity into the second position P2, the inclined surface 56 of the ring 52 engages with the second ends 74 of the locking elements 74. Hereby, the locking elements 72 are pivoted radially inwardly toward the needle guard 30 until the locking elements 72 are reaching their locking position LP. In this locking position LP the second ends 74 of the locking elements 72 are in engagement with the recess, the undercut, the step 36, or the like of the needle guard 30 which is locked in its position relative to the outer body 20.

The locking mechanism 70 is therefore not only actuated by the detecting element 50, but also controlled, because as long as the medicament delivery device is held in this wrong position, the detecting element 50 secures the locking elements 72 in their locking position LP.

Only when the medicament delivery device 10 is held in the correct orientation, the ring 52 slips back by the gravity into the first position P1 and the locking elements 72 can swing back into their release position LP.

To support this, in a further embodiment, the locking elements 72 may be applied with a force, in particular with a reset force which is preferably directed radially outwardly with respect to the needle guard 30.

One can see that the locking mechanism 70, in particular the locking elements 72 are movable within the outer body 20 between a release position RP and a locking position LP, wherein the locking mechanism 70 takes the release position RP, if the detecting element 50 is in the first position P1, and wherein the locking mechanism 70 takes the locking position LP, if the detecting element 50 is in the second position P2.

In another embodiment, the orientation safeguarding, with its control and locking mechanism, comprising a detecting element 50 for the detection of the orientation of the medicament delivery device 10, and with a locking mechanism 70 releasing or locking the needle guard 30 of the medicament delivery device 10, could be applied to other medicament delivery devices such as safety syringes.

In an exemplary embodiment the orientation safeguarding system could be applied to devices with moving syringes as well. This would presumably involve the locking mechanism 70, in particular the locking elements 72 locking the syringe movement.

The terms "medicament" in this application is used synonymously and describes a pharmaceutical formulation containing one or more active pharmaceutical ingredients or pharmaceutically acceptable salts or solvates thereof, and optionally a pharmaceutically acceptable carrier.

An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A medicament may be used for a limited duration, or on a regular basis for chronic disorders.

As described below, a medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The medicament may be contained in a primary package or medicament receptacle or container adapted for use with the medicament delivery device 10. The medicament container may be, e.g., a cartridge, syringe, reservoir, or other solid or flexible vessel configured to provide a suitable chamber for storage (e.g., short- or long-term storage) of one or more medicaments or drugs.

For example, in some instances, the receptacle or chamber may be designed to store a drug for at least one day (e.g., 1 to at least 30 days). In some instances, the chamber may be designed to store a medicament or drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing.

Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, ora human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

All features and advantages resulting from the claims, the description and the drawings, including design details, spatial arrangements and method steps may be essential to the invention both in itself and in a variety of combinations.

However, one recognizes that the present invention relates to a medicament delivery device, comprising an outer body, a receptacle for a medicament, a needle for the administration of the medicament, an injection mechanism with an actuating mechanism for injecting the medicament into the patient's body, and a needle guard for the needle. The medicament delivery device further comprising a detecting element for the detection of the orientation of the medicament delivery device, and a locking mechanism releasing the injection mechanism and/or the actuating mechanism and/or the needle guard, if the detecting element is in the at least first position, and locking the injection mechanism and/or the actuating mechanism and/or the needle guard, if the detecting element is in the at least second position, wherein the locking mechanism is controlled and/or actuated by the detecting element.

Mechanical ratchets 72 prohibit an activation of the device 10 if the device 10 is held in wrong orientation. These ratchets 72 are built-in in the autoinjector 10.

FIG. 1 shows the bottom part of the device 10 in correct orientation and the needle guard 30 with the movable ratchets 72. The needle guard 30 can be pressed in by pressing the device 10 against the skin S.

If the user holds the device 10 in a wrong orientation the gravity moves the detecting element 50 downwards (FIG. 2).

The ring 52 presses the ratchets 72 against the needle guard 30 and fixes them in this position. The ratchets 72 are active now and prohibit the needle guard 30 to be pressed and the device 10 can't be activated.

The invention claimed is:

1. A medicament delivery device comprising:
   an outer body;
   a receptacle for a medicament to be administered;
   a needle for administration of the medicament into a patient's body;
   a needle guard for the needle, a distal end of the needle guard having a needle opening for the needle ; and
   an actuating mechanism for moving the needle or the receptacle or the needle guard in an axial direction of the medicament delivery device;
   a detecting element for detecting an orientation of the medicament delivery device the detecting element being movable between at least a first position and at least a second position,
   wherein the detecting element takes the at least first position, if the medicament delivery device is held in an orientation in which the medicament delivery device is usable for injecting the medicament into the patient's body, and
   wherein the detecting element takes the at least second position, if the medicament delivery device is held in an orientation that is not suitable for usage or is in a configuration not intended for use in injecting the medicament into the patient's body; and
   a locking mechanism releasing the actuating mechanism, if the detecting element is in the at least first position, and locking the actuating mechanism, if the detecting element is in the at least second position, wherein the locking mechanism is movable between a release position and a locking position , wherein the locking mechanism takes the release position, if the detecting element is in the at least first position, wherein the locking mechanism takes the locking position, if the detecting element is in the at least second position,
   wherein the locking mechanism has at least one locking element, each of the at least one locking element being movable between the release position and the locking position,
   wherein each of the at least one locking element is a detent, a ratchet or a latch, wherein each of the at least one locking element is mounted rotatably or pivotally within or at the outer body,
   wherein the actuating mechanism has a recess, an undercut or a step for an engagement of, or for receiving each of the at least one locking element, wherein each of the at least one locking element is in engagement with the recess, the undercut or the step, when the at least one locking element has been moved into the locking position, and
   wherein the detecting element is a collar or a ring, and wherein the detecting element is driven or moved by gravity.

2. The medicament delivery device of claim 1, wherein the locking mechanism, in the release position, is not engaged with the actuating mechanism, and the locking mechanism, in the locking position, is engaged with the actuating mechanism.

3. The medicament delivery device of claim 1, wherein the locking mechanism is controlled or actuated by the detecting element.

4. The medicament delivery device of claim 1, wherein each of the at least one locking element is brought into its respective locking position and into engagement with the actuating mechanism by the detecting element.

5. The medicament delivery device of claim 1, wherein the detecting element has an opening with a face, which interacts with the at least one locking element, when the detecting element moves from the at least first position to the at least second position.

6. The medicament delivery device of claim 1, wherein the detecting element, in the at least second position, encloses the at least one locking element in their locking position.

7. The medicament delivery device of claim 1, wherein the receptacle and the needle form a syringe, the syringe being movable by the actuating mechanism in the axial direction of the medicament delivery device, wherein the needle guard for the needle is an integral part of the outer body, and the needle opening for the needle is at the distal end of the outer body.

8. The medicament delivery device of claim 1, wherein the medicament delivery device is an autoinjector.

9. The medicament delivery device of claim 1, wherein the needle guard is a part of the actuating mechanism and is movable in the axial direction relative to the outer body, wherein the locking mechanism releases a movement of the needle guard, if the detecting element is in the at least first position, and locks the movement of the needle guard, if the detecting element is in the at least second position.

10. A system comprising:
   a medicament delivery device comprising:
      an outer body;
      a needle for administration of a medicament into a patient's body;
      a needle guard for the needle, the needle guard having a needle opening for the needle at a distal end; and
      an actuating mechanism for moving the needle or the needle guard in an axial direction of the medicament delivery device;
      a detecting element for the detection of an orientation of the medicament delivery device the detecting element being movable between at least a first position and at least a second position,
      wherein the detecting element takes the at least first position, if the medicament delivery device is held in the orientation in which the medicament delivery device is usable for injecting the medicament into the patient's body, and
      wherein the detecting element takes the at least second position, if the medicament delivery device is held in an orientation that is not suitable for usage or is in a configuration not intended for use in injecting the medicament into the patient's body; and
      a locking mechanism releasing the actuating mechanism, if the detecting element is in the at least first position, and locking the actuating mechanism, if the detecting element is in the at least second position, wherein the locking mechanism is movable between a release position and a locking position, wherein the locking mechanism takes the release position, if the detecting element is in the at least first position, wherein the locking mechanism takes the locking position, if the detecting element is in the at least second position,
      wherein the locking mechanism has at least one locking element, each of the at least one locking element being movable between the release position and the locking position,
      wherein each of the at least one locking element is a detent, a ratchet or a latch, wherein each of the at least one locking element is mounted rotatably or pivotally within or at the outer body,
      wherein the actuating mechanism has a recess, an undercut or a step for an engagement of, or for receiving each of the at least one locking element, wherein each of the at least one locking element is in engagement with the recess, the undercut or the step, when the at least one locking element has been moved into the locking position, and
      wherein the detecting element is a collar or a ring, and wherein the detecting element is driven or moved by gravity, and
   a receptacle, comprising a primary container, mounted in the medicament delivery device, wherein the primary container is filled with the medicament to be administered.

11. The system of claim 10, wherein the locking mechanism, in the release position, is not engaged with the actuating mechanism, and the locking mechanism, in the locking position, is engaged with the actuating mechanism.

12. The system of claim 10, wherein the locking mechanism is controlled or actuated by the detecting element.

13. The system of claim 10, wherein each of the at least one locking element is brought into its respective locking position and into engagement with the actuating mechanism by the detecting element.

14. The system of claim 10, wherein the detecting element has an opening with a face, which interacts with the at least one locking element, when the detecting element moves from the at least first position to the at least second position.

15. The system of claim 10, wherein the detecting element, in the at least second position, encloses the at least one locking element in their locking position.

16. A method comprising:
   triggering an actuating mechanism for moving a needle or a needle guard of a medicament delivery device in an axial direction of the medicament delivery device;
   detecting an orientation of the medicament delivery device by detecting a movement of a detecting element between at least a first position and at least a second position, wherein the detecting element takes the at least first position, if the medicament delivery device is held in the orientation in which the medicament delivery device is usable for injecting a medicament into the patient's body, and wherein the detecting element takes the at least second position, if the medicament delivery device is held in an orientation that is not suitable for usage or is in a configuration not intended for use in injecting the medicament into the patient's body, wherein the detecting element is a collar or a ring, and wherein the detecting element is driven or moved by gravity;
   determining whether the detecting element is in the at least first position or in the at least second position; and
   in response to determining that the detecting element is in the at least first position, releasing, by a locking mechanism, an actuating mechanism, wherein the locking mechanism is movable between a release position and a locking position and the locking mechanism takes the release position, if the detecting element is in the at least first position, wherein the locking mechanism comprises at least one locking element, each of the at least one locking element being movable between the release position and the locking position, wherein each of the at least one locking element is a detent, a ratchet or a latch, wherein each of the at least one locking element is mounted rotatable or pivotally within or at the outer body; or in response to determining that the detecting element is in the at least second position, locking the actuating mechanism, wherein the locking mechanism takes the locking position, if the detecting element is in the at least second position, wherein the actuating mechanism has a recess, an undercut or a step for an engagement of, or for receiving each of the at least one locking element, wherein each of the at least one locking element is engaged with the recess, the undercut or the step, when the at least one locking element has been moved into the locking position.

17. The method of claim 16, wherein each of the at least one locking element is brought into its respective locking position and into engagement with the actuating mechanism by the detecting element.

18. The method of claim 16, wherein determining whether the detecting element is in the at least first position or in the at least second position comprises: detecting an interaction between an opening face of the detecting element and the at least one locking element.

19. The method of claim 16, wherein determining that the detecting element is in the at least second position comprises enclosing the at least one locking element in respective locking positions.

20. The method of claim 16, further comprising releasing a needle guard movement, if the detecting element is in the at least first position, and locking the needle guard movement, if the detecting element is in the at least second position.

\* \* \* \* \*

UNITED STATES PATENT AND TRADEMARK OFFICE
CERTIFICATE OF CORRECTION

| | |
|---|---|
| PATENT NO. | : 11,844,936 B2 |
| APPLICATION NO. | : 17/253705 |
| DATED | : December 19, 2023 |
| INVENTOR(S) | : Stephan Riedel |

It is certified that error appears in the above-identified patent and that said Letters Patent is hereby corrected as shown below:

On the Title Page

Column 2 (Item (57) Abstract), Line 5, delete "patients" and insert -- patient's --

In the Claims

Column 14, Line 12, Claim 1, delete "needle ;" and insert -- needle; --

Column 14, Line 35, Claim 1, delete "position ," and insert -- position, --

Column 15, Line 58, Claim 10, delete "position ," and insert -- position, --

Signed and Sealed this
First Day of October, 2024

Katherine Kelly Vidal
*Director of the United States Patent and Trademark Office*